(12) United States Patent
Klunder et al.

(10) Patent No.: US 9,708,641 B2
(45) Date of Patent: Jul. 18, 2017

(54) MOBILE APP FOR CHEMICAL DETECTION

(71) Applicant: Lawrence Livermore National Security, LLC, Livermore, CA (US)

(72) Inventors: Gregory Klunder, Oakland, CA (US); Chadway R. Cooper, Corvallis, OR (US); Joe H. Satcher, Jr., Patterson, CA (US); Ephraim A. Tekle, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 652 days.

(21) Appl. No.: 13/742,536

(22) Filed: Jan. 16, 2013

(65) Prior Publication Data

US 2014/0080129 A1 Mar. 20, 2014

Related U.S. Application Data (60) Provisional application No. 61/646,518, filed on May 14, 2012.

(51) Int. Cl.
*G01N 21/78* (2006.01)
*C12Q 1/68* (2006.01)

(52) U.S. Cl.
CPC .............. *C12Q 1/68* (2013.01); *G01N 21/78* (2013.01)

(58) Field of Classification Search
CPC .................................................... G01N 21/78
USPC ..... 436/43, 46, 50, 106, 107, 110, 127, 135, 436/164–166, 171, 172; 422/68.1, 78–80, 422/83, 86, 87, 400, 402, 403; 73/35.15–35.17
See application file for complete search history.

(56) References Cited

U.S. PATENT DOCUMENTS

| | | | | |
|---|---|---|---|---|
| 6,096,205 A | * | 8/2000 | Haas | G01N 30/90 210/198.3 |
| 7,771,653 B2 | * | 8/2010 | Del Eckels | G01N 21/78 422/400 |
| 7,834,320 B2 | * | 11/2010 | Goldberg | G01N 21/78 250/338.5 |
| 8,071,385 B2 | * | 12/2011 | Haas | G01N 1/4022 422/400 |
| 8,669,115 B2 | * | 3/2014 | Pagoria et al. | 436/164 |
| 8,999,129 B2 | * | 4/2015 | Jung | B01D 43/00 204/450 |
| 9,222,126 B2 | * | 12/2015 | Bearinger | C12Q 1/6844 |
| 2005/0064601 A1 | * | 3/2005 | Haas | G01N 30/90 436/162 |
| 2006/0216833 A1 | * | 9/2006 | Pagoria | B01L 3/5023 436/514 |
| 2009/0221085 A1 | * | 9/2009 | Pagoria | G01N 30/94 436/162 |
| 2009/0293589 A1 | | 12/2009 | Freund et al. | |

(Continued)

OTHER PUBLICATIONS

Ann Parker, "Pocket-Sized test Detects," S& TR pp. 16-17, Oct. 2006.

*Primary Examiner* — Peter Macchiarolo
*Assistant Examiner* — Hoang Nguyen
(74) *Attorney, Agent, or Firm* — Eddie E. Scott (57) ABSTRACT

The present invention incorporates the camera from a mobile device (phone, iPad, etc.) to capture an image from a chemical test kit and process the image to provide chemical information. A simple user interface enables the automatic evaluation of the image, data entry, gps info, and maintain records from previous analyses.

5 Claims, 8 Drawing Sheets

(56) References Cited

U.S. PATENT DOCUMENTS

2009/0297135 A1* 12/2009 Willner .................. G03B 17/00
396/153
2011/0149056 A1* 6/2011 Dugan .................... H04W 4/02
348/61
2011/0239745 A1* 10/2011 Satcher, Jr. ............ G01N 30/90
73/61.55
2012/0057741 A1* 3/2012 Macklin .................. G01N 1/02
382/100

* cited by examiner

MOBILE APP FOR CHEMICAL DETECTION

CROSS-REFERENCE TO RELATED APPLICATIONS

This application claims benefit under 35 U.S.C. §119(e) of U.S. Provisional Patent Application No. 61/646,518 filed May 14, 2012 entitled "Mobile App for Chemical Detection," the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

Field of Endeavor

The present invention relates to chemical detection and more particularly to a mobile app for chemical detection.

State of Technology

U.S. Published Patent Application No. 2006/0216833 for a spot test kit for explosives detection provides the state of technology information reproduced below. U.S. Published Patent Application No. 2006/0216833 is incorporated into this application in its entirety for all purposes by this reference.

The preset invention provides an inspection tester system for testing a suspect surface for explosives. The system includes the step of providing a lateral flow membrane swab unit; providing a first explosives detecting reagent; providing a second explosives detecting reagent; swiping the suspect surface with the lateral flow membrane swab unit, delivering the first explosives detecting reagent to the lateral flow membrane swab unit, wherein if the lateral flow membrane swab unit becomes colored the test is positive for explosives and if no color appears the test for explosives is negative to this point; and delivering the second explosives detecting reagent to the lateral flow membrane swab unit, wherein if the lateral flow membrane swab unit becomes colored the test is positive for explosives and if no color appears the test for explosives is negative. The inspection tester system comprises a body, a lateral flow membrane swab unit adapted to be removable connected to the body, a first explosives detecting reagent, a first reagent holder and dispenser operatively connected to the body, the first reagent holder and dispenser containing the first explosives detecting reagent and positioned to deliver the first explosives detecting reagent to the lateral flow membrane swab unit when the lateral flow membrane swab unit is connected to the body, a second explosives detecting reagent, and a second reagent holder and dispenser operatively connected to the body, the second reagent holder and dispenser containing the second explosives detecting reagent and positioned to deliver the second explosives detecting reagent to the lateral flow membrane swab unit when the lateral flow membrane swab unit is connected to the body.

STEP 1) A suspect surface is swiped with the removable swab unit sample pad 401. This may be accomplished by the swab unit sample pad 401 being swiped across a surface containing the suspect substance or the swab unit pad 401 may be exposed to the suspect substance in other ways such as adding the suspect substance to the swab unit sample pad 401. This will cause any explosives residue to be colleted and held by the swab unit sample pad 401.

STEP 2) The breakable or squeezable ampoule A 408 is located in a position to deliver the first explosives detecting reagent A to the lateral flow membrane 411. The breakable or squeezable ampoule A 408 is pressed to break or squeeze it thereby dispensing reagent A onto the lateral flow membrane 411. The regent A contacts any explosives residue that has been collected by the swab unit sample pad 401. The lateral flow membrane 411 concentrates suspect materials along the solvent front. If the swab unit sample pad 401 becomes colored, the test is positive for explosives. If no color appears the test for explosives is negative to this point.

STEP 3) If STEP 2 is negative to this point, the breakable or squeezable ampoule B 409 is pressed to brake or squeeze it thereby dispensing reagent B onto the lateral flow membrane 411. The breakable or squeezable ampoule B 409 is located in a position to deliver the second explosives detecting reagent B to the lateral flow membrane 411. The regent B contacts any explosives residue that has been collected by the swab unit sample pad 401. The lateral flow membrane 411 concentrates suspect materials along the solvent front. If the swab unit sample pad 401 becomes colored, the test is positive for explosives. If no color appears the test for explosives is negative to this point.

STEP 4) If STEP 3 is negative to this point, the breakable or squeezable ampoule C 410 is pressed to brake or squeeze it thereby dispensing reagent C onto the lateral flow membrane 411. The breakable or squeezable ampoule C 410 is located in a position to deliver the second explosives detecting reagent C to the lateral flow membrane 411. The regent C contacts any explosives residue that has been collected by the swab unit sample pad 401. The lateral flow membrane 411 concentrates suspect materials along the solvent front. If the swab unit sample pad 401 becomes colored, the test is positive for explosives. If no color appears the test for explosives is negative to this point.

STEP 5) If any of the various STEPS 2, 3, and 4 are negative and greater sensitivity is desired, the inspection tester 400 can be positioned in a heating unit. This causes the swab unit sample pad 401, reagents A, B, and/or C and any explosives residue to become heated. If the swab unit sample pad 401 now becomes colored, the test is positive for explosives. If no color appears the test for explosives is negative.

U.S. Pat. No. 7,771,653 for an explosives tester with heater provides the state of technology information reproduced below. U.S. Pat. No. 7,771,653 is incorporated into this application in its entirety for all purposes by this reference.

The present invention provides an inspection tester system for testing for explosives. The system comprises a body, a swab unit adapted to be removeably connected to the body, at least one explosives detecting reagent, at least one reagent holder and dispenser operatively connected to the body, the at least one reagent holder and dispenser containing the at least one explosives detecting reagent and positioned to deliver the at least one explosives detecting reagent to the swab unit, and a heater operatively connected to the body, wherein the swab unit is adapted to be operatively connected to the heater.

In one embodiment, the at least one explosives detecting reagent is the Griess reagent. The key to some of the explosive testing kits described above is the Griess reagent. Known since 1879, the Griess reagent reacts with nitrogen oxide compounds, whether bound or free, and produces a highly colored compound that can be used for visible detection. This compound has been shown to be an effective indicator for not only high explosives, but other source of nitrogen oxides, such as biological systems. The inspection tester 100 uses a simple and rapid procedure summarized by the following four step operation:

STEP 1) A suspect surface is swiped with the removable swab unit sample pad 104. This may be accomplished by the swab unit sample pad 104 being swiped across a surface containing the suspect substance or the swab unit pad 104 may be exposed to the suspect substance in other ways such as adding the suspect substance to the swab unit sample pad 104. This will cause any explosives residue to be collected and held by the swab unit sample pad 104.

STEP 2) The breakable or squeezable ampoule A 106 is located in a position to deliver the first explosives detecting reagent A to the color reaction area 112 of the removable swab unit 104. The breakable or squeezable ampoule A 106 is pressed to break or squeeze it thereby dispensing reagent A onto the color reaction area 112 of the removable swab unit 104. The regent A contacts any explosives residue that has been collected by the swab unit sample pad 104. The color reaction area 112 of the removable swab unit 104 concentrates suspect materials along the solvent front. If the swab unit sample pad 104 becomes colored, the test is positive for explosives. If no color appears the test for explosives is negative to this point.

STEP 3) If STEP 2 is negative to this point, the heater 102 is activated. This causes the swab unit sample pad 104, reagent A, and any explosives residue to become heated. If the swab unit sample pad 104 now becomes colored, the test is positive for explosives. If no color appears the test for explosives is negative to this point.

STEP 4) The breakable or squeezable ampoule B 107 is located in a position to deliver the second explosives detecting reagent B to the color reaction area 112 of the removable swab unit 104. If STEP 3 is negative to this point, the breakable or squeezable ampoule B 107 is pressed to brake or squeeze it thereby dispensing reagent B onto the color reaction area 112 of the removable swab unit 104. The regent B contacts any explosives residue that has been collected by the swab unit sample pad 104. The color reaction area 112 of the removable swab unit 104 concentrates suspect materials along the solvent front. If the swab unit sample pad 104 becomes colored, the test is positive for explosives. If no color appears the test for explosives is negative to this point.

STEP 5) If STEP 4 is negative to this point, the heater 102 is activated. This causes the swab unit sample pad 104, reagent B, and any explosives residue to become heated. If the swab unit sample pad 104 now becomes colored, the test is positive for explosives. If no color appears the test for explosives is negative.

U.S. Pat. No. 6,096,205 for a hand portable thin-layer chromatography system provides the following state of the art information reproduced below. U.S. Pat. No. 6,096,205 is incorporated into this application in its entirety for all purposes by this reference.

Various analytical techniques are used to measure the type and amount of contamination from unknown chemicals in environmental, industrial, civilian, and military situations. Conventional thin-layer chromatography (TLC) analysis is routinely used in analytical laboratories worldwide for quantitative and qualitative characterization of unknowns. This technique is ideal for rapid pre-screening and identification of known and unknown chemicals. TLC allows multiple samples and standards (in mg to ng quantities) to be chromatographed simultaneously on a TLC plate in a solvent tank. Semiquantitative and qualitative assessment from all samples is then readily obtained by inspection of the plates, which may be chemically developed and then illuminated to display the separated components (appearing as spots). Further quantitative analysis may be performed using an illumination box, camera, and data acquisition equipment. Unfortunately, conventional TLC apparatus is cumbersome, typically made of glass, and is not field-deployable or field-ruggedized for on-site analysis. Current TLC hardware is not hand portable when including all the necessary support equipment such as plates, tanks, solvent, pipettes, ruler, etc. Furthermore, the illumination and data acquisition equipment needed to fully analyze samples is oversized and extremely heavy. Thus, there is a need for a hand portable, field-ready TLC system, including data acquisition capability, that is cost-effective and efficient for analyzing multiple samples of unknown chemicals on-site in a variety of emergency and non-emergency situations.

The article "Pocket-Sized Test Detects Trace Explosives" in the October 2006 issue of *Science & Technology Review* describes the Easy Livermore Inspection Test for Explosives (ELITE) and provides the state of technology information below.

SECURITY forces throughout the world need detection tools that can quickly and accurately locate small amounts of explosives. Technology developed by Lawrence Livermore will provide emergency response, law-enforcement, and military personnel with an easy-to-use explosives detector small enough to carry in a shirt pocket. This technology, called E.L.I.T.E.™ (Easy Livermore Inspection Test for Explosives), is inexpensive and requires minimal training for deployment.

Although, the eye is a good detector it is subjective and has limitations in different lighting conditions. The application will also be able to more specifically identify color using the 3 different color channels of the camera (image).

Simple field portable chemical detection test kits have been developed at LLNL and licensed by companies for sale. These include Easy Livermore Inspection Test for Explosives (ELITE) and a mini thin-layer chromatography (mini-TLC) separation system. The ELITE works by wiping a surface and adding chemicals to react with and colorize any explosives that might be present. In mini-TLC, a sample is spotted on a plate and then placed in a solvent that wicks up the plate and separates the chemicals in the sample based on interactions with the solvent and surface material. The chemicals separate into unique bands and are detected by quenching of fluorescence from the plate or adding a reagent to colorize the compounds.

Both ELITE and TLC normally rely on visual inspection to detect and identify the chemicals present. Using a camera to take an image will provide a more permanent record of the results and enable more objective evaluation through software. The best way to make this amenable to the field user is to provide an application to devices (e.g. cell phones) that are already there.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention incorporates the camera from a mobile device (phone, iPad, etc.) to capture an image from a chemical test kit and process the image to provide chemical information. Field detection chemical tests, such as TLC or ELITE, normally rely on visual inspection for evaluation. This app will enable the user to evaluate band location, color, and provide enhanced sensitivity compared to visual analysis. A simple user interface enables the automatic evaluation of the image, data entry, gps info, and maintain records from previous analyses. The application will compare band location in TLC to a standard or predetermined migration times, compare colors from different colorimetric tests, and provide more sensitive detection of the colors for improved sensitivity. The application could be used on mobile devices such as cell phones, iPad, or iPods.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF SPECIFIC EMBODIMENTS

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Prior art chemical tests normally rely on visual inspection to detect and identify the chemicals present. The present invention incorporates the camera from a mobile device (phone, iPad, etc.) to capture an image from a chemical test kit and process the image to provide chemical information. Using the camera to take an image will provide a more permanent record of the results and enable more objective evaluation through software. The present invention will make chemical tests amenable to the field user is to provide an application to devices (e.g. cell phones) that are already there.

The mobile app will provide a way to analyze images and determine which compounds are present compared to standards. Thin layer chromatography, TLC, is a separation method that separates chemicals based on their interaction with the solvent and stationary phase material. Samples spotted on the bottom of a plate will migrate up with the solvent as it wicks toward the top due to capillary action. Different chemicals move at different rates and have unique retention factors, Rf. Based on the Rf and/or comparison to standards on the same plate, the chemicals can be identified.

This application takes an image of the TLC plate and finds the bands and identifies the compounds based on a library of Rf values and/or comparing to standards on the plate. Detection is normally achieved visually however using image analysis provides a more objective analysis, provides an archived image, and generates a database of analyses for future reference. Information about the samples can be entered, saved and searched. Based on the chemicals detected additional information can be provided to the field user, e.g. type of explosive formulation, safety info, where has it been detected previously, etc.

Detection of the bands, chemical locations, can be achieved by indirect fluorescence or colorimetric. For indirect fluorescence, the TLC plate contains a fluorescing compound that is quenched due to the presence of the other chemicals separated on the plate, which appear as dark bands against a green background. Some chemicals can be detected directly if they are colored or by dipping/spraying the plate with a reactive compound that results in colored analytes. The coloring step adds extra information for identification and the application will be able to evaluate the different colors as well.

Other chemical detection kits, e.g. ELITE, do not rely on separation but do provide a color reaction. This application will enhance the color compared to the background to provide greater sensitivity. Although, the eye is a good detector it is subjective and has limitations in different lighting conditions. The application will also be able to more specifically identify color using the 3 different color channels of the camera (image).

The present invention will be further explained, illustrated, and described in the following examples of systems of the present invention. The examples demonstrate the utility and/or function of the invention and help provide a full describe of the invention. The examples are intended to be illustrative and not limitative of the present invention.

EXAMPLE 1

Tests for Explosives

Figure 1:
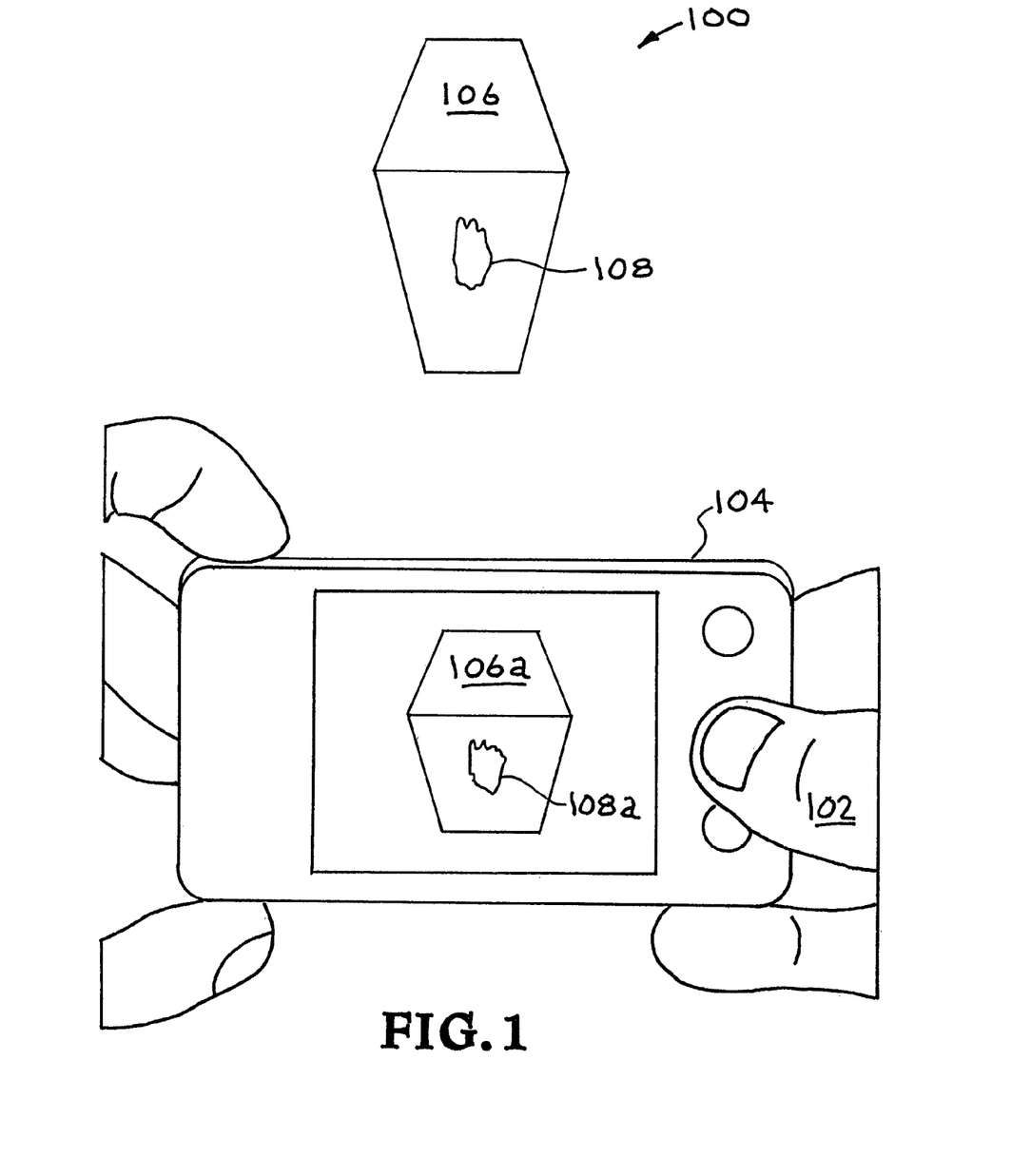
FIG. 1 illustrates a mobile app system for determining the presence of explosives using a mobile device with a camera and computing capabilities.
Figure 2A:
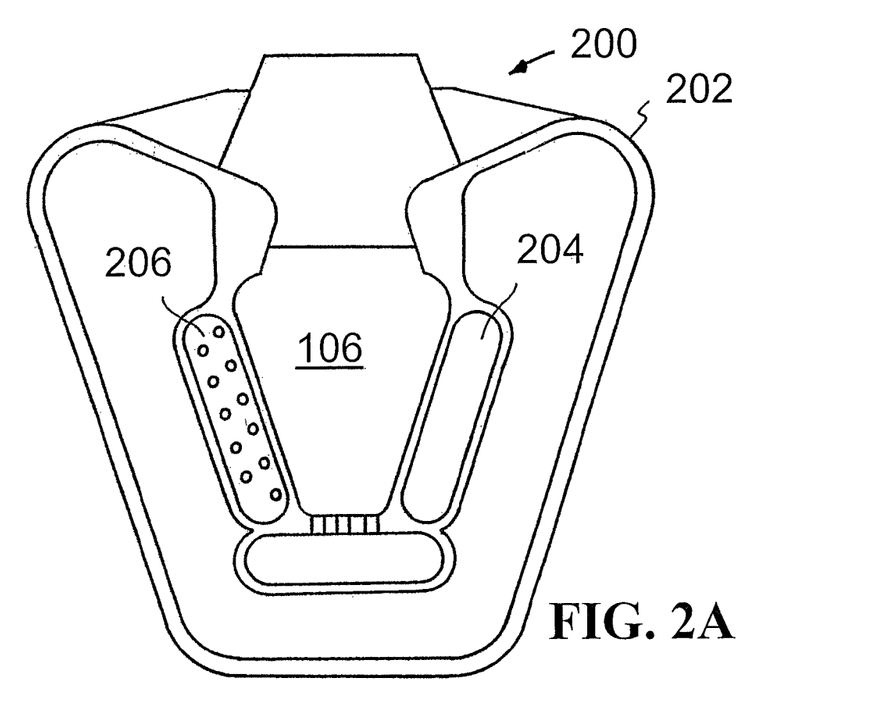
FIGS. 2A and 2B illustrate an inspection tester kit with removable swab unit sample pad.
Figure 2B:
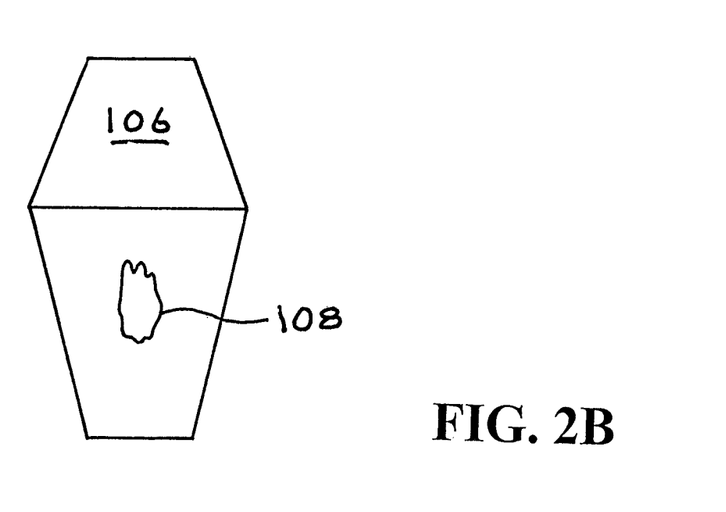

Referring now to the drawings and in particular to FIGS. 1, 2A, and 2B, a mobile app system for providing chemical information of the present invention is illustrated. The mobile app system for determining the presence of explosives using a mobile device with a camera and computing capabilities is illustrated in FIG. 1. The mobile app system is designated generally by the reference numeral 100. In mobile app system 100, a test to determine the presence of explosives has been performed producing results 108. The camera of the mobile device 104 has been used by an individual 102 for capturing an image 106a/108a of said results. The computing capabilities of the mobile device 104 are used for processing the image 106a/108a to provide information on the presence of explosives.

Referring now to FIGS. 2A and 2B, an inspection tester kit with removable swab unit sample pad 106 is illustrated. The inspection tester kit is designated generally by the reference numeral 200. The inspection tester kit 200 includes an explosives tester body 202 and removable swab unit 106. The swab unit 106 is adapted to be removably positioned in the explosives tester body 202. A breakable or squeezable ampoule A 204 and a breakable or squeezable ampoule B 206 are located in the explosives tester body 202 adjacent the removable swab unit 106.

A suspect surface has been swiped with the removable swab unit sample pad 106 of the inspection tester kit 200. The swab unit sample pad 106 has been saturated with detecting reagent from breakable or squeezable ampoule A 204 and/or breakable or squeezable ampoule B 206 or both. The protocol of the inspection tester kit 200 dictates that if the swab unit sample pad 106 becomes colored the test is positive for explosives and if no color appears the test for explosives is negative.

As illustrated in FIG. 2B, a colored patch 108 on the swab unit sample pad 106 has appeared and the test is positive for explosives. The inspection tester kit 200 provides a small, disposable, one use system. The inspection tester kit 200 uses a simple and rapid method of operation. The removable swab unit sample pad 106 is shown separately in FIG. 2B. The removable swab unit sample pad 106 is exposed to a suspect substance. This may be accomplished by the swab unit sample pad 106 being swiped across a surface containing the suspect substance or the swab unit pad 106 may be exposed to the suspect substance in other ways such as adding the suspect substance to the swab unit sample pad 106. The swab unit sample pad 106 is then placed in the inspection tester body 202 for testing a sample as shown in FIG. 2A.

Referring again to FIG. 2A, the explosives tester body 202 is a thin flat body that can be described as a card. The card body 202 is made of a suitable material such as paper, wood, plastic, glass, or other suitable material. The explosives tester body 202 is thin and is less than one fourth inch thick. The explosives tester body 202 shown in FIG. 2A is less than one fourth inch thick. The explosives tester body 202 includes a docking entry and retention portion for easy docking of the removable swab unit sample pad 106. The explosives tester body 202 includes ampoule A 204 and ampoule B 206. In various embodiments, ampoule A 204 and ampoule B 206 are breakable ampoules, breakable glass ampoules, squeezable ampoules, and other types of ampoules. As illustrated in FIG. 2A, ampoule B 206 includes indentations on the chamber which keeps glass pieces from adhering to the walls. The inspection tester kit 200 uses a simple and rapid procedure summarized by the following three step operation:

STEP 1) A suspect surface is swiped with the removable swab unit sample pad 106. This may be accomplished by the swab unit sample pad 106 being swiped across a surface containing the suspect substance or the swab unit pad 106 may be exposed to the suspect substance in other ways such as adding the suspect substance to the swab unit sample pad 106. This will cause any explosives residue to be collected and held by the swab unit sample pad 106.

STEP 2) The breakable or squeezable ampoule A 204 is located in a position to deliver the first explosives detecting reagent A to the color reaction area of the removable swab unit 106. The breakable or squeezable ampoule A 204 is pressed to break or squeeze it thereby dispensing reagent A onto the color reaction area of the removable swab unit 106. The regent A contacts any explosives residue that has been collected by the swab unit sample pad 106. The color reaction area of the removable swab unit 106 concentrates suspect materials along the solvent front. If the swab unit sample pad 106 becomes colored, the test is positive for explosives. If no color appears the test for explosives is negative to this point.

STEP 3) If STEP 2 is negative to this point, the breakable or squeezable ampoule B 206 is located in a position to deliver the second explosives detecting reagent B to the color reaction area of the removable swab unit 106. If STEP 2 is negative to this point, the breakable or squeezable ampoule B 206 is pressed to brake or squeeze it thereby dispensing reagent B onto the color reaction area of the removable swab unit 106. The regent B contacts any explosives residue that has been collected by the swab unit sample pad 106. The color reaction area of the removable swab unit 106 concentrates suspect materials along the solvent front. If the swab unit sample pad 106 becomes colored, the test is positive for explosives. If no color appears the test for explosives is negative.

Referring again to FIG. 2B, the swab unit sample pad 106 is shown separately. A colored patch 108 on the swab unit sample pad 106 has appeared and the test is positive for explosives. Referring again to FIG. 1, an individual 102 is shown taking a picture of the swab unit sample pad 106 and the colored patch 108 on the swab unit sample pad 106 using a cell phone 104 having a camera feature.

The picture of the swab unit sample pad 106 and the colored patch 108 on the swab unit sample pad 106 has been taken with the camera feature of the cell phone 104. The mobile app system 100 of the present invention provides processing of the image to provide confirm the presence of explosives. The image of the colored patch 108s on the swab unit sample pad 106a confirms the presence of explosives. Had no image been present the test for explosives would have been negative.

Field detection chemical tests, such as explosives detection tests, normally rely on visual inspection for evaluation. The mobile app system of the present invention will enable the user to evaluate band location, color, and provide enhanced sensitivity compared to visual analysis. A simple user interface enables the automatic evaluation of the image, data entry, gps info, and maintain records from previous analyses. The mobile app system 100 can be used on mobile devices such as cell phones, cell pad, cell pods, and other mobile devices.

EXAMPLE 2

Spray Test for Explosives

Figure 3:
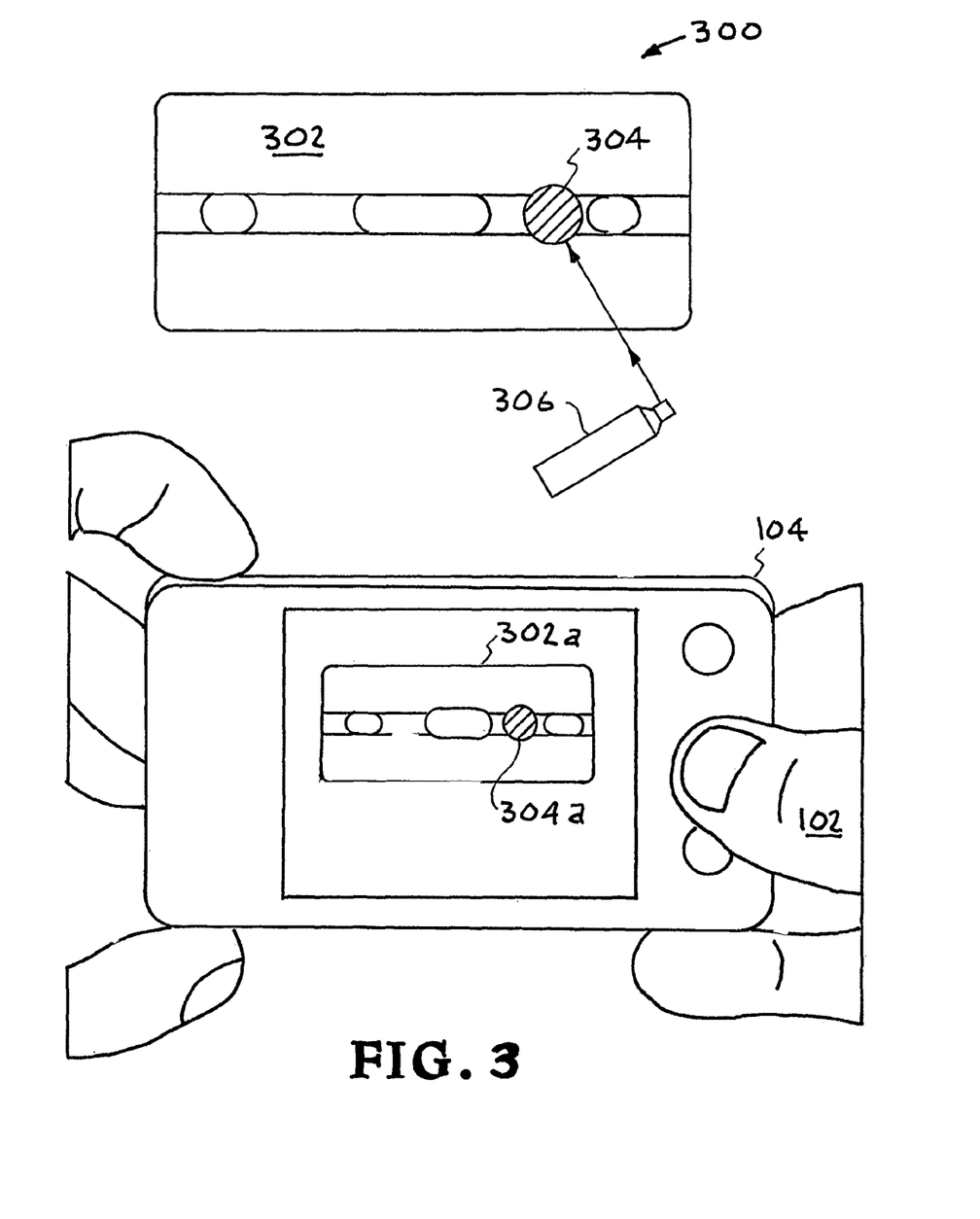
FIG. 3 illustrates another example of an embodiment of a mobile app system for providing chemical information of the present invention.

Referring now to FIG. 3, another example of an embodiment of a mobile app system for providing chemical information of the present invention is illustrated. This embodiment of the present invention is a mobile app spray test for explosives system. The mobile app spray test for explosives system is designated generally by the reference numeral 300.

The system 300 is illustrated in FIG. 3. An individual 102 is shown taking a picture of a suitcase 302 and a colored patch 304 on the suitcase 302 using a cell phone 104 having a camera feature and computing capabilities. In system 300, a test to determine the presence of explosives has been performed producing results 304 in the form of a colored patch 304 on the suitcase 302. The camera of the mobile device 104 has been used by an individual 102 for capturing an image 302a of the suitcase 302 and an image 304a of the results 304 in the form of a colored patch. The computing capabilities of the mobile device 104 are used for processing the image 302a/304a to provide information on the presence of explosives.

A suspect surface on the suitcase 302 has been sprayed with an explosives detection spray 306. The protocol of the explosives detection spray 306 dictates that if a colored patch appears on the sprayed area the test is positive for explosives and if no colored patch appears the test for explosives is negative. As illustrated in FIG. 3, a colored patch 304 on the suitcase 302 has appeared and the test is positive for explosives.

Referring again to FIG. 3, an individual 102 is shown taking a picture of the suitcase 302 and the colored patch 304 on the suitcase 302 using a cell phone 104 having a camera feature and computing capabilities. The picture of the suitcase 302 and the colored patch 304 on the suitcase 306 has been taken with the camera feature of the cell phone 104. The mobile app system 300 of the present invention provides processing of the image to provide confirm the presence of explosives. The image 304a of the colored patch on the suitcase 302a confirms the presence of explosives. Had no image been present the test for explosives would have been negative.

Field detection chemical tests, such as explosives detection tests, normally rely on visual inspection for evaluation. The mobile app system of the present invention will enable the user to evaluate band location, color, and provide enhanced sensitivity compared to visual analysis. A simple user interface enables the automatic evaluation of the image, data entry, gps info, and maintain records from previous analyses. The mobile app system 300 can be used on mobile devices such as cell phones, cell pad, cell pods, and other mobile devices.

Advantages of Mobile App Swipe Pad Test for Explosives System 300

Although, the eye is a good detector it is subjective and has limitations in different lighting conditions. The application will also be able to more specifically identify color using the 3 different color channels of the camera (image). Some of the advantages of the mobile app system of the present invention include the following advantages:

(1) cameras are more sensitive than the human eye,
(2) cell phones with cameras are ubiquitous,
(3) image enhancements can improve detection limits,
(4) the image can be compared with a standard,
(5) the image can be stored and cataloged to provide documentation,
(6) the image and relevant information can be geo-tagged.
(7) the mobile app system 100 enables the user to evaluate band location, color, and provide enhanced sensitivity compared to visual analysis.
(8) a simple user interface enables the automatic evaluation of the image, data entry, gps info, and maintain records from previous analyses.

(9) The application will compare band location to a standard or predetermined migration times, compare colors from different colorimetric tests, and provide more sensitive detection of the colors for improved sensitivity.

EXAMPLE 3

Documentation of Explosives Detection Test Results

Figure 4:
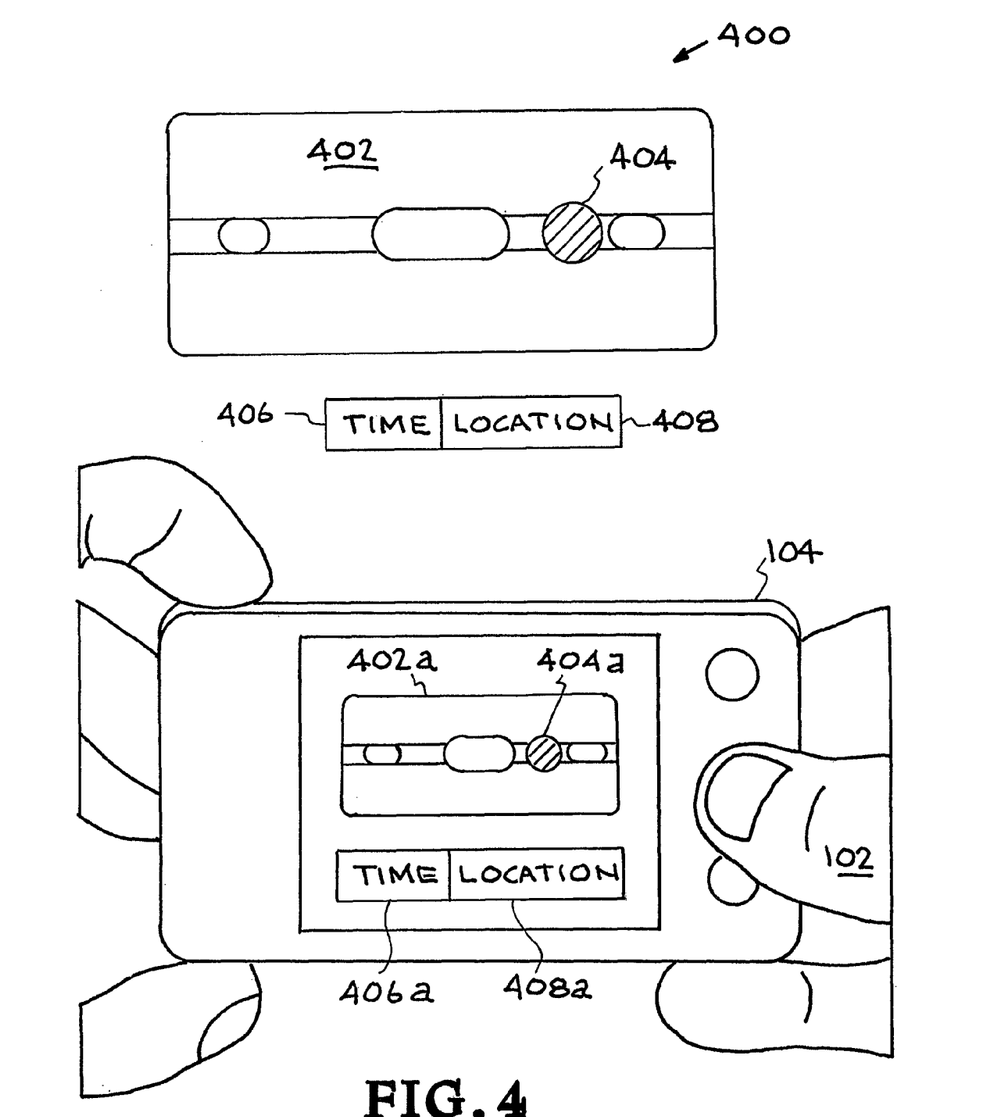
FIG. 4 illustrates a mobile app system for documentation of tests for explosives.

Referring now FIG. 4, one embodiment of a mobile app system for providing chemical information of the present invention is illustrated. This embodiment of the present invention is a mobile app system for documentation of tests for explosives. The system is designated generally by the reference numeral 400.

An individual 102 is shown taking a picture of a suitcase 402 and a colored patch 404 on suitcase 402 using a cell phone 104 having a camera feature and computing capabilities. In system 400, a test to determine the presence of explosives has been performed producing results 404 in the form of a colored patch 404 on the suitcase 402. The camera of the mobile device 104 has been used by an individual 102 for capturing an image 402a of the suitcase 402 and an image 404a of the results 404 in the form of a colored patch. The computing capabilities of the mobile device 104 are used for processing the image 402a/404a to provide information on the presence of explosives.

The mobile device 104 stores the image 402a/404a to provide documentation of the test. The mobile device 104 can also store the time 406 and location 408. This is generally illustrated by the images 406a and 406b; however, it is understood that electronic storage of time and location can be accomplished electronically by well know system.

EXAMPLE 4

Thin Layer Chromatography System

Figure 5:
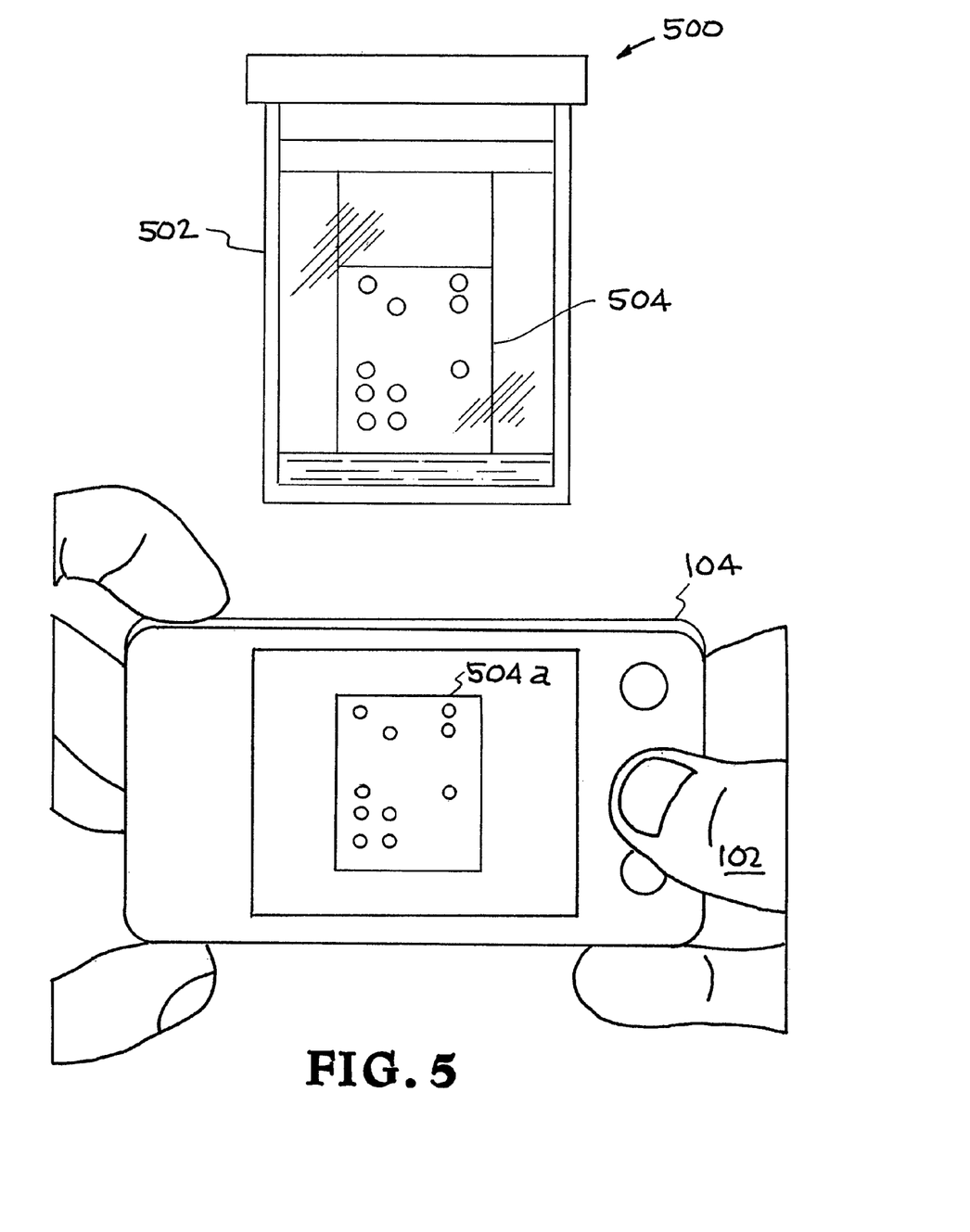
FIG. 5 illustrates another example of an embodiment of a mobile app system for providing chemical information of the present invention.

Referring now to FIG. 5, another example of an embodiment of a mobile app system for providing chemical information of the present invention is illustrated. This embodiment of the present invention is a mobile app thin layer chromatography system. The mobile app thin layer chromatography system is designated generally by the reference numeral 500. An individual 102 is shown taking a picture of a thin layer chromatography device 502 and a plate 504 in the thin layer chromatography device 502 using a cell phone 104 having a camera feature and computing capabilities.

In thin layer chromatography system 500, an individual 102 is shown taking a picture of the thin layer chromatography device 502 and a plate 504 in the thin layer chromatography device using a cell phone 104 having a camera feature and computing capabilities. The picture of the thin layer chromatography device 502 and a plate 504 in the thin layer chromatography device has been taken with the camera feature of the cell phone 104. The mobile app system 500 of the present invention provides processing of the image 504a.

Thin layer chromatography (TLC) is a chromatography technique used to provide chemical information. Thin layer chromatography is performed on a sheet of glass, plastic, or aluminium foil, which is coated with a thin layer of adsorbent material, usually silica gel, aluminium oxide, or cellulose (blotter paper). This layer of adsorbent is known as the stationary phase. After the sample to be tested has been applied on the plate, a solvent or solvent mixture (known as the mobile phase) is drawn up the plate via capillary action. Because different analytes ascend the TLC plate at different rates, separation is achieved.

Thin layer chromatography can be used to monitor the progress of a reaction, identify compounds present in a given mixture, and determine the purity of a substance. Specific examples of these applications include: analyzing ceramides and fatty acids, detection of pesticides or insecticides in food and water, analyzing the dye composition of fibers in forensics, assaying the radiochemical purity of radiopharmaceuticals, or identification of medicinal plants and their constituents.

To run a thin layer chromatography test, the following procedure is used:

A small spot of solution containing the sample is applied to a plate, about 1.5 centimeters from the bottom edge. The solvent is allowed to completely evaporate off, otherwise a very poor or no separation will be achieved. If a non-volatile solvent was used to apply the sample, the plate needs to be dried in a vacuum chamber.

A small amount of an appropriate solvent (elutant) is poured in to a glass beaker or any other suitable transparent container (separation chamber) to a depth of less than 1 centimeter. A strip of filter paper (aka "wick") is put into the chamber, so that its bottom touches the solvent, and the paper lies on the chamber wall and reaches almost to the top of the container. The container is closed with a cover glass or any other lid and is left for a few minutes to let the solvent vapors ascend the filter paper and saturate the air in the chamber. (Failure to saturate the chamber will result in poor separation and non-reproducible results).

The TLC plate is then placed in the chamber so that the spot(s) of the sample do not touch the surface of the elutant in the chamber, and the lid is closed. The solvent moves up the plate by capillary action, meets the sample mixture and carries it up the plate (elutes the sample). When the solvent front reaches no higher than the top of the filter paper in the chamber, the plate should be removed and dried.

Different compounds in the sample mixture travel at different rates due to the differences in their attraction to the stationary phase, and because of differences in solubility in the solvent. By changing the solvent, or perhaps using a mixture, the separation of components (measured by the Rf value) can be adjusted.

In organic chemistry, reactions are qualitatively monitored with TLC. Spots sampled with a capillary tube are placed on the plate: a spot of starting material, a spot from the reaction mixture, and a "co-spot" with both. A small (3 by 7 cm) TLC plate takes a couple of minutes to run. The analysis is qualitative, and it will show if the starting material has disappeared, i.e. the reaction is complete, if any product has appeared, and how many products are generated.

EXAMPLE 5

Electrophoresis Analysis System

Figure 6:
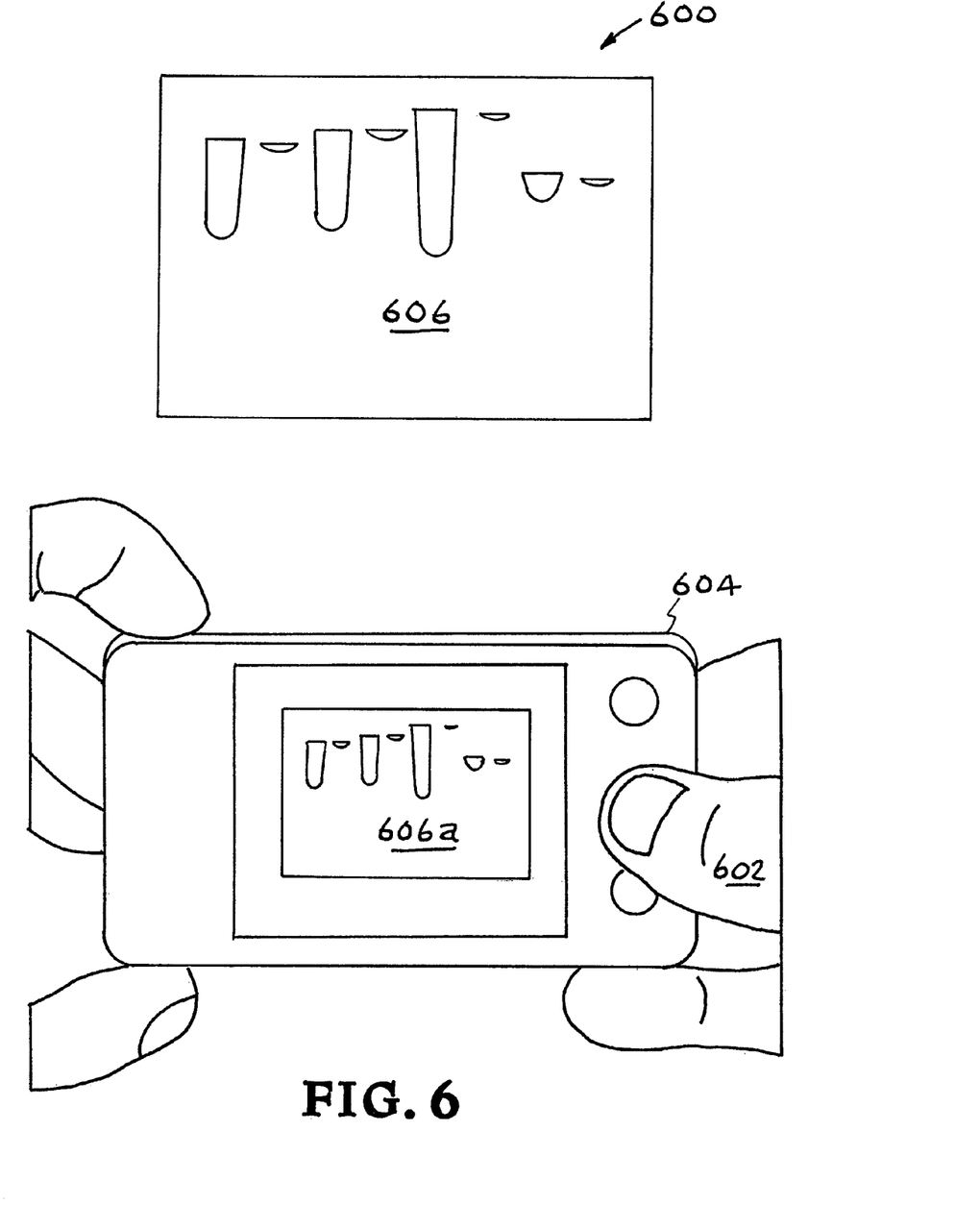
FIG. 6 illustrates a mobile app electrophoresis analysis system.

Referring now to FIG. 6, another example of an embodiment of a mobile app analysis system for providing chemical information of the present invention is illustrated. This embodiment of the present invention is a mobile app electrophoresis analysis system. The mobile app electrophoresis analysis system is designated generally by the reference numeral 600. An individual 602 is shown taking a picture of an electrophoresis gel 606 using a cell phone 604 having a camera feature and computing capabilities.

In electrophoresis analysis system 600, an individual 602 is shown taking a picture of the electrophoresis gel 606 using a cell phone 604 having a camera feature and computing capabilities. The picture of the electrophoresis gel 606 has been taken with the camera feature of the cell phone 604. The mobile app analysis system 600 of the present invention provides processing of the image 606a.

Electrophoresis is a technique used to provide chemical information. In simple terms: Electrophoresis is a process which enables the sorting of molecules based on size. Using an electric field, molecules (such as DNA) can be made to move through a gel made of agar or polyacrylamide. The molecules being sorted are dispensed into a well in the gel material. The gel is placed in an electrophoresis chamber, which is then connected to a power source. When the electric current is applied, the larger molecules move more slowly through the gel while the smaller molecules move faster. The different sized molecules form distinct bands on the gel.

The term "gel" in this instance refers to the matrix used to contain, then separate the target molecules. In most cases, the gel is a crosslinked polymer whose composition and porosity is chosen based on the specific weight and composition of the target to be analyzed. When separating proteins or small nucleic acids (DNA, RNA, or oligonucleotides) the gel is usually composed of different concentrations of acrylamide and a cross-linker, producing different sized mesh networks of polyacrylamide. When separating larger nucleic acids (greater than a few hundred bases), the preferred matrix is purified agarose. In both cases, the gel forms a solid, yet porous matrix. Acrylamide, in contrast to polyacrylamide, is a neurotoxin and must be handled using appropriate safety precautions to avoid poisoning. Agarose is composed of long unbranched chains of uncharged carbohydrate without cross links resulting in a gel with large pores allowing for the separation of macromolecules and macromolecular complexes.

"Electrophoresis" refers to the electromotive force (EMF) that is used to move the molecules through the gel matrix. By placing the molecules in wells in the gel and applying an electric field, the molecules will move through the matrix at different rates, determined largely by their mass when the charge to mass ratio (Z) of all species is uniform, toward the (negatively charged) cathode if positively charged or toward the (positively charged) anode if negatively charged.

If several samples have been loaded into adjacent wells in the gel, they will run parallel in individual lanes. Depending on the number of different molecules, each lane shows separation of the components from the original mixture as one or more distinct bands, one band per component. Incomplete separation of the components can lead to overlapping bands, or to indistinguishable smears representing multiple unresolved components. Bands in different lanes that end up at the same distance from the top contain molecules that passed through the gel with the same speed, which usually means they are approximately the same size. There are molecular weight size markers available that contain a mixture of molecules of known sizes. If such a marker was run on one lane in the gel parallel to the unknown samples, the bands observed can be compared to those of the unknown in order to determine their size. The distance a band travels is approximately compared against standard or markers and analysis are mostly done with specialized software.

Depending on the type of analysis being performed, other techniques are often implemented in conjunction with the results of gel electrophoresis, providing a wide range of field-specific applications.

Electrophoresis is used in clinical chemistry to separate proteins by charge and or size (IEF agarose, essentially size independent) and in biochemistry and molecular biology to separate a mixed population of DNA and RNA fragments by length, to estimate the size of DNA and RNA fragments or to separate proteins by charge. Nucleic acid molecules are separated by applying an electric field to move the negatively charged molecules through an agarose matrix. Shorter molecules move faster and migrate farther than longer ones because shorter molecules migrate more easily through the pores of the gel.

This phenomenon is called sieving. Proteins are separated by charge in agarose because the pores of the gel are too large to sieve proteins. Gel electrophoresis can also be used for separation of nanoparticles.

Gel electrophoresis uses a gel as an anticonvective medium and or sieving medium during electrophoresis, the movement of a charged particle in an electrical field. Gels suppress the thermal convection caused by application of the electric field, and can also act as a sieving medium, retarding the passage of molecules; gels can also simply serve to maintain the finished separation, so that a post electrophoresis stain can be applied. DNA Gel electrophoresis is usually performed for analytical purposes, often after amplification of DNA via PCR, but may be used as a preparative technique prior to use of other methods such as mass spectrometry, RFLP, PCR, cloning, DNA sequencing, or Southern blotting for further characterization.

EXAMPLE 6

DNA Analysis System

Figure 7:
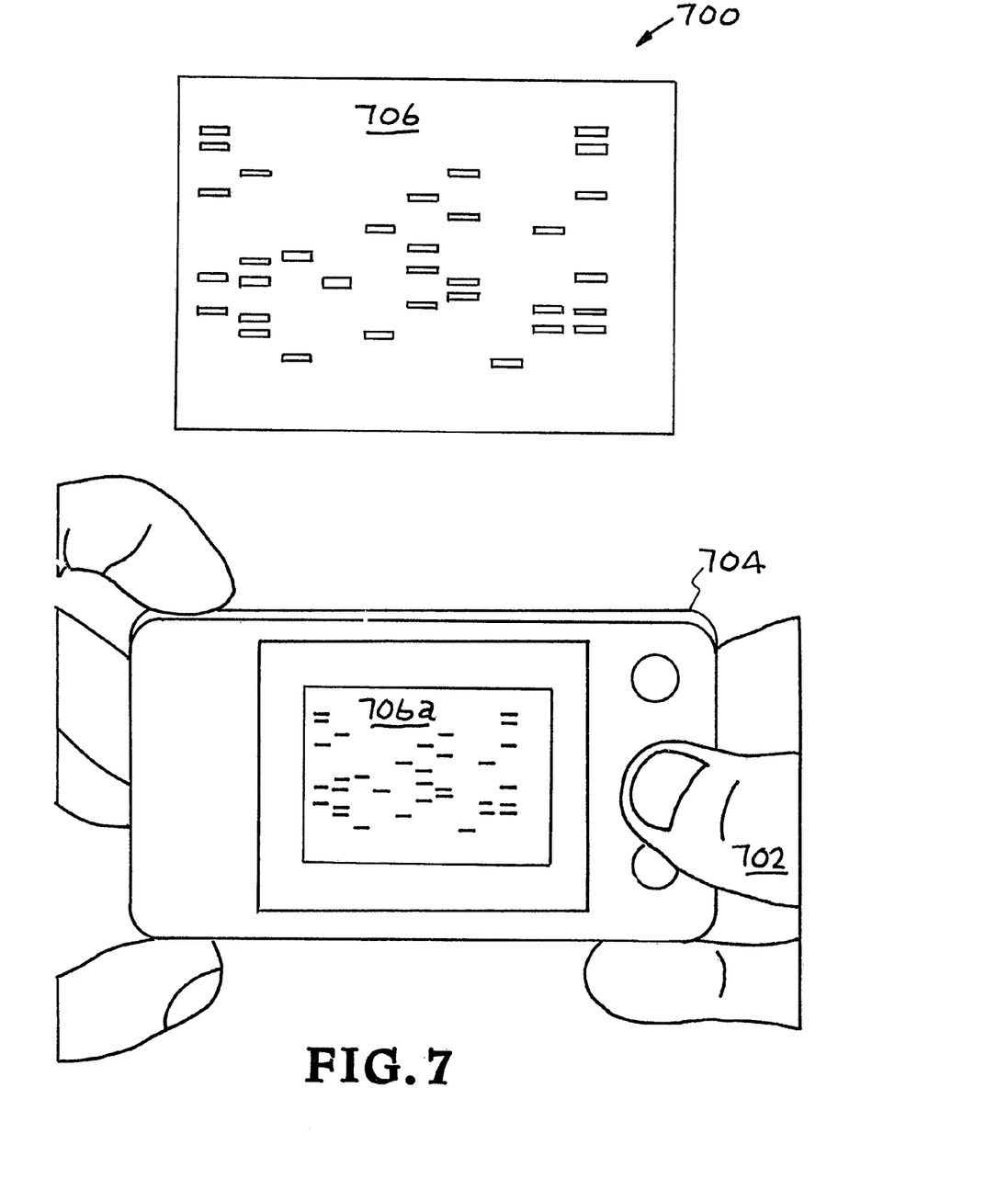
FIG. 7 illustrates a mobile app DNA analysis system.

Referring now to FIG. 7, another example of an embodiment of a mobile app analysis system for providing chemical information of the present invention is illustrated. This embodiment of the present invention is a mobile app DNA analysis system. The mobile app DNA analysis system is designated generally by the reference numeral 700. An individual 702 is shown taking a picture of a DNA test result 706 using a cell phone 704 having a camera feature and computing capabilities.

In DNA analysis system 700, an individual 702 is shown taking a picture of the DNA test result 706 using a cell phone 704 having a camera feature and computing capabilities. The picture of the DNA test result 706 has been taken with the camera feature of the cell phone 704. The mobile app analysis system 700 of the present invention provides processing of the image 706*a*.

DNA testing is a technique used to provide chemical information. DNA testing is a technique employed by forensic scientists to assist in the identification of individuals by their respective DNA profiles. DNA profiles are encrypted sets of numbers that reflect a person's DNA makeup, which can also be used as the person's identifier.

The process begins with a sample of an individual's DNA (typically called a "reference sample"). The most desirable method of collecting a reference sample is the use of a buccal swab, as this reduces the possibility of contamination. When this is not available other methods may need to be used to collect a sample of blood, hair root, saliva, semen. or other appropriate fluid or tissue from personal items (e.g. toothbrush, razor, etc.) or from stored samples (e.g. banked sperm or biopsy tissue). Samples obtained From blood relatives (biological relative) can provide an indication of an individual's profile, as could human remains which had been previously profiled.

A reference sample is then analyzed to create the individual's DNA profile using one of a number of techniques, discussed below. The DNA profile is then compared against another sample to determine whether there is a genetic match.

EXAMPLE 7

Networking Test Results & Databases

Figure 8:
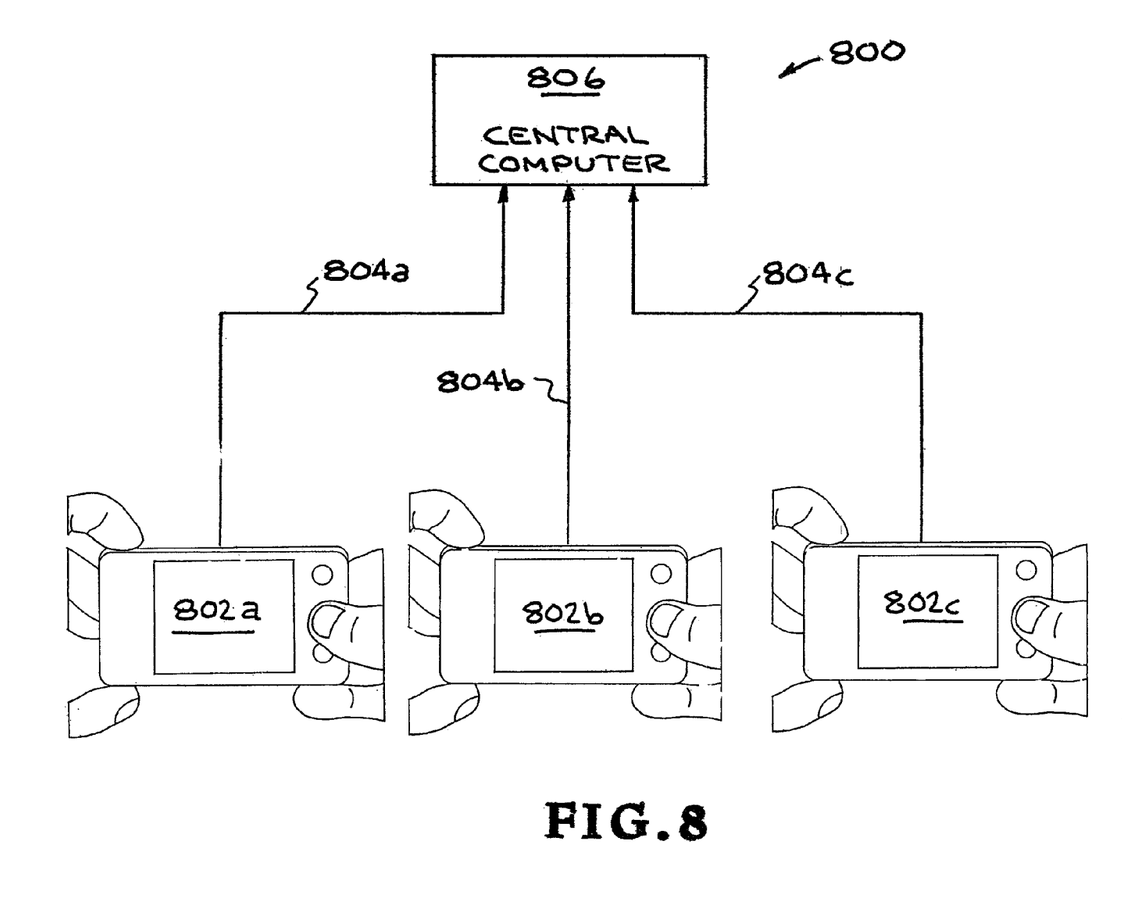
FIG. 8 illustrates a mobile app system networking test results and creating data bases.

Referring now FIG. 8, one embodiment of a mobile app system for providing chemical information of the present invention is illustrated. This embodiment of the present invention is a mobile app system networking test results and creating data bases. The system is designated generally by the reference numeral 800.

Individuals are shown taking pictures of chemical information test results using cell phones having a camera features and computing capabilities as indicated at 802*a*, 802*b*, and 802*c*. The mobile devices store the image to provide documentation of the test. The mobile device can also store the time and location. The mobile device transmits the information to a central computer 806. This transmission is illustrated by the arrows 804*a*, 804*b*, and 804*c* respectively.

A test result database can be used in the analysis of chemical information for many purposes. The databases may be public or private. These databases are held electronically in the central computer 806. The test result database are created by cell phones having a camera features and computing capabilities as indicated at 802*a*, 802*b*, and 802*c* transmitting results of chemical information tests.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A test for determining the presence of explosives residue on a suspect surface, comprising the steps of:
   providing an explosives tester having a tester body, a removable sample pad, and a breakable or squeezable ampoule containing an explosives detecting reagent;
   removing said removable sample pad from said tester body;
   swiping said removable sample pad on the suspect surface to collect said explosives residue;
   positioning said removable sample pad with said explosives residue in said tester body proximate said breakable or squeezable ampoule containing said explosives detecting reagent;
   squeezing or breaking said breakable or squeezable ampoule containing said explosives detecting reagent dispensing said explosives detecting reagent onto said removable sample pad with said explosives residue producing a color reaction with said explosives residue and a color on said removable sample pad;
   providing a cell phone having a camera feature, different color channels, storage capability, time determination capability, and a global positioning system capability;
   taking a picture of said removable sample pad with said color on said removable sample pad with said cell phone having said camera feature, different color channels, storage capability, time determination capability, and a global positioning system capability thereby capturing an image of said color; and using said cell phone having said camera feature, different color channels, storage capability, time determination capability, and a global positioning system capability for processing said image of said removable sample pad with said color on said removable sample pad to determine whether said color reaction indicates the presence of explosives residue on the suspect surface;

wherein said cell phone having said camera feature, different color channels, storage capability, time determination capability, and a global positioning system capability for processing said image of said removable sample pad with said color on said removable sample pad includes a standard from different colorimetric tests;

using said standard from different colorimetric tests to compare said color reaction with said standard to provide confirmation of the presence of explosives residue on the suspect surface, and storing said image and time of said sample pad with said color using said cell phone having said camera feature, different color channels, storage capability, time determination capability, time determination capability, and a global positioning system capability thereby providing documentation of the presence of explosives residue on the suspect surface.

2. The A test for determining the presence of explosives residue on a suspect surface, comprising the steps of:

providing an explosives tester having a tester body, a removable sample pad, and a breakable or squeezable ampoule containing an explosives detecting reagent;

removing said removable sample pad from said tester body;

swiping said removable sample pad on the suspect surface to collect said explosives residue;

positioning said removable sample pad with said explosives residue in said tester body proximate said breakable or squeezable ampoule containing said explosives detecting reagent;

squeezing or breaking said breakable or squeezable ampoule containing said explosives detecting reagent dispensing said explosives detecting reagent onto said removable sample pad with said explosives residue producing a color reaction with said explosives residue and a color on said removable sample pad;

providing a cell phone having a camera feature, different color channels, storage capability, time determination capability, and a global positioning system capability wherein said step of providing a cell phone having said camera feature, different color channels, storage capability, time determination capability, and a global positioning system capability includes providing a cell phone having said camera feature with three different color channels, taking a picture of said removable sample pad with said color on said removable sample pad with said cell phone having said camera feature, different color channels, storage capability, time determination capability, and a global positioning system capability thereby capturing an image of said color wherein said step of taking a picture of said removable sample pad with said color on said removable sample pad with said cell phone having said camera feature, different color channels, storage capability, time determination capability, and a global positioning system capability thereby capturing an image of said color comprises taking a picture of said removable sample pad with said color on said removable sample pad with said cell phone having said camera feature with three different color channels thereby capturing an image of said color using said three different color channels, using said cell phone having said camera feature, different color channels, storage capability, time determination capability, and a global positioning system capability for processing said image of said removable sample pad with said color on said removable sample pad to provide confirmation of the presence of explosives residue on the suspect surface wherein said step of using said cell phone having, different color channels, storage capability, time determination capability, and a global positioning system capability for processing said image of said color to provide confirmation of the presence of explosives residue on the suspect surface comprises using said cell phone having said camera feature with three different color channels for processing said image of said color to determine whether said color reaction indicates the presence of explosives residue on the suspect surface, wherein said cell phone having said camera feature, different color channels, storage capability, time determination capability, and a global positioning system capability for processing said image of said removable sample pad with said color on said removable sample pad includes a standard from different colorimetric tests, using said standard from different colorimetric tests to compare said color reaction with said standard to provide confirmation of the presence of explosives residue on the suspect surface, and storing said image and time of said sample pad with said color using said cell phone having said camera feature, different color channels, storage capability, time determination capability, time determination capability, and a global positioning system capability thereby providing documentation of the presence of explosives residue on the suspect surface.

3. A thin layer chromatography test for determining components of a sample, comprising the steps of:

providing a thin layer chromatography plate by providing a thin layer chromatography plate having a gel;

placing the sample on said thin layer chromatography plate by providing a thin layer chromatography plate having a gel;

placing said thin layer chromatography plate and the sample in a chamber containing eluent to determine the presence of the components of the sample when the components are moved up said thin layer chromatography plate by capillary action;

drying said thin layer chromatography plate with the components moved up said thin layer chromatography plate;

providing a cell phone having a camera feature, storage capability and time determination capability;

using said camera feature of said cell phone for capturing an image of said components to determine whether said components have moved up said thin layer chromatography plate;

wherein said cell phone for capturing an image of said components to determine whether said components have moved up said thin layer chromatography plate includes a standard;

using said standard to provide confirmation said components have moved up said thin layer chromatography plate; and using said cell phone having a camera feature, storage capability and time determination capability for processing said image to store said image and time.

4. An electrophoresis analysis method for providing chemical information using molecules of a sample, comprising:

providing an electrophoresis gel;

placing the sample on said electrophoresis gel;

placing said electrophoresis gel with the sample in an electrophoresis chamber wherein the molecules of the sample move through the gel;

providing a cell phone having a camera feature, storage capability and time determination capability;

using said camera feature of said cell phone for capturing an image of said molecules of the sample in said gel;

using said cell phone having a camera feature, storage capability and time determination capability of said cell phone for processing said image to provide the chemical information;

wherein said cell phone having a camera feature, storage capability and time determination capability includes a standard;

using said standard to provide confirmation of said chemical information; and using said storage capability and time determination capability of said cell phone for providing storage of said image of said molecules of the sample in said gel.

5. A spray test for testing a suspect surface for the presence of explosives residue associated with a location, comprising the steps of:

spraying the suspect surface with an explosives detection spray to determine the presence of explosives residue on a the suspect surface producing a color on the suspect surface indicating the presence of explosives residue on the suspect surface at the location, providing a cell phone having a camera feature, different color channels, storage capability and time determination capability;

using said cell phone having a camera feature for capturing an image of said color on the suspect surface, processing said image of said color on the suspect surface using said different color channels, storage capability and time determination capability of said cell phone to provide confirmation of the presence of explosives residue on the suspect surface;

wherein said cell phone having a camera feature, different color channels, storage capability and time determination capability includes a standard from different colorimetric tests;

using said standard from different colorimetric tests to compare said color reaction with said standard to provide confirmation of the presence of explosives residue on the suspect surface;

processing said image of said color on the suspect surface to provide information of the presence of the explosives residue on the suspect surface and using said storage capability and time determination capability of said cell phone to store said image of said color on the suspect surface together with a time determination of said image of said color on the suspect surface, and using said different color channels, storage capability and time determination capability of said cell phone for providing documentation of said image of said color on the suspect surface together with said time determination of said image of said color on the suspect surface.

* * * * *